United States Patent [19]
Guire et al.

[11] Patent Number: 6,020,147
[45] Date of Patent: *Feb. 1, 2000

[54] CHEMICAL ANALYSIS APPARATUS AND METHOD

[75] Inventors: Patrick E. Guire, Eden Prairie; Melvin J. Swanson, Carver, both of Minn.

[73] Assignee: SurModics, Inc., Eden Prairie, Minn.

[*] Notice: This patent is subject to a terminal disclaimer.

[21] Appl. No.: 07/891,864

[22] Filed: Jun. 1, 1992

Related U.S. Application Data

[60] Continuation of application No. 07/574,607, Aug. 28, 1990, abandoned, which is a division of application No. 06/467,229, Feb. 23, 1983, Pat. No. 5,073,484, which is a continuation of application No. 06/356,459, Mar. 9, 1982, abandoned.

[51] Int. Cl.[7] ................... G01N 33/543; G01N 33/558; G01N 33/566
[52] U.S. Cl. ................... 435/7.92; 435/7.94; 435/7.95; 435/970; 436/501; 436/514; 436/518; 436/810
[58] Field of Search ................... 435/7.92, 7.94, 435/7.95, 970; 436/514, 518, 810, 501; 422/56

[56] References Cited

U.S. PATENT DOCUMENTS

| | | | |
|---|---|---|---|
| 3,420,205 | 1/1969 | Morison | 422/56 |
| 3,437,449 | 4/1969 | Luckey | 436/167 |
| 3,475,129 | 10/1969 | Peurifoy et al. | 422/60 |
| 3,798,004 | 3/1974 | Zerachia et al. | 422/56 |
| 3,811,840 | 5/1974 | Bauer et al. | 422/56 |
| 3,868,219 | 2/1975 | Hurenkamp | 436/530 |
| 3,981,981 | 9/1976 | Reunanen | 436/535 |
| 4,018,662 | 4/1977 | Ruhenstroh-Bauer et al. | 422/58 |
| 4,046,514 | 9/1977 | Johnston | 422/56 |
| 4,059,407 | 11/1977 | Hochstrasser | 422/56 |
| 4,094,647 | 6/1978 | Deutsch et al. | 422/56 |
| 4,116,638 | 9/1978 | Kenoff | 422/99 |
| 4,145,186 | 3/1979 | Andersen | 422/57 |
| 4,168,146 | 9/1979 | Grubb et al. | 422/56 |
| 4,189,304 | 2/1980 | Adams, Jr. et al. | 422/56 |
| 4,235,601 | 11/1980 | Deutsch et al. | 436/514 |
| 4,258,001 | 3/1981 | Pierce et al. | 422/56 |
| 4,274,832 | 6/1981 | Wu et al. | 422/56 |
| 4,347,312 | 8/1982 | Brown et al. | 435/7 |
| 4,366,241 | 12/1982 | Tom et al. | 435/7 |
| 4,374,925 | 2/1983 | Litman et al. | 435/7 |

(List continued on next page.)

FOREIGN PATENT DOCUMENTS

| | | |
|---|---|---|
| 48-5925 | 1/1973 | Japan . |
| 53-6465 | 2/1978 | Japan . |
| 54-135633 | 3/1978 | Japan . |
| 55-159155 | 12/1980 | Japan . |
| 1547688 | 11/1977 | United Kingdom . |

OTHER PUBLICATIONS

Glad et al., "The Use of Enzyme–labeled Antibodies to Increase the Sensitivity of Immunocapillarymigration", Acta Chem. Scand. 6:449–450 (1980).

Glad et al., Anal. Bioch. 85:180 (1978).

Norgard–Pederson, Clinica Chemica Acta 48:345 (1973).

Laurell et al. in Methods in Enzymology, vol. 73, Part B, p. 339 et seq. (1981).

Isamu Takeda et al., "Experience in Use of Urotrace for Urine of Patients", received Oct. 1, 1973.

Primary Examiner—David Saunders
Attorney, Agent, or Firm—Fredrikson & Byron, P.A.

[57] ABSTRACT

A method and apparatus for the quantitative determination of an analyte in a liquid employs a liquid-permeable solid medium defining a liquid flow path. The medium includes a number of reactant-containing reaction zones spaced apart along the flow path and in which reaction occurs with the analyte or an analyte derivative (e.g., a labeled analyte) to result in the formation of a predetermined product. Detector means are employed to detect analyte, analyte derivative, reactant or predetermined product in the reaction zones, the number of such zones in which such detection occurs indicating the amount of analyte in the liquid.

12 Claims, 2 Drawing Sheets

U.S. PATENT DOCUMENTS

| | | | |
|---|---|---|---|
| 4,425,438 | 1/1984 | Bauman et al. | 436/527 |
| 4,435,504 | 3/1984 | Zuk et al. | 435/7 |
| 4,442,204 | 4/1984 | Greenquist et al. | 435/7 |
| 4,444,193 | 4/1984 | Fogt et al. | 422/56 |
| 4,446,232 | 5/1984 | Liotta et al. | 435/7 |
| 4,447,526 | 5/1984 | Rupchock et al. | 435/7 |
| 4,459,358 | 7/1984 | Berke | 436/170 |
| 4,517,288 | 5/1985 | Giegel et al. | 435/7 |
| 4,552,839 | 11/1985 | Gould et al. | 435/7 |
| 4,690,907 | 9/1987 | Hibino et al. | 436/514 |
| 4,861,711 | 8/1989 | Friesen et al. | 436/514 |
| 5,073,484 | 12/1991 | Swanson et al. | 435/7.92 |
| 5,141,875 | 8/1992 | Kelton et al. | 436/514 |
| 5,654,162 | 8/1997 | Guire et al. | |

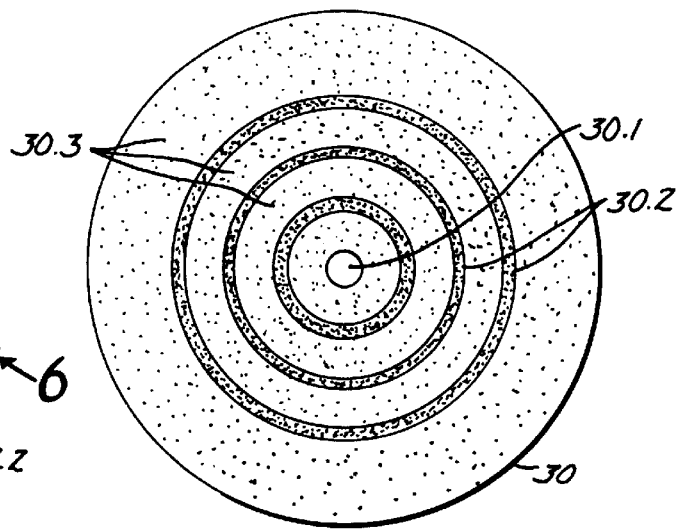
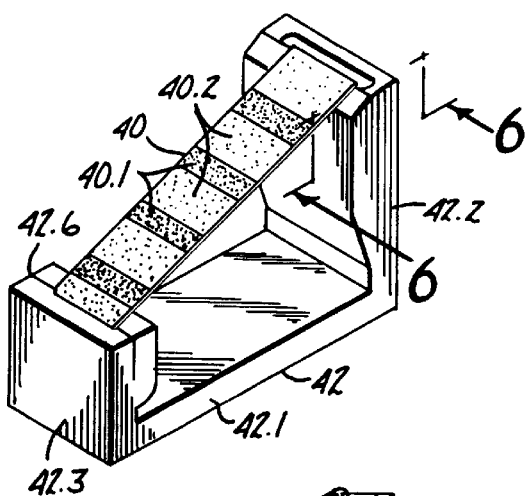
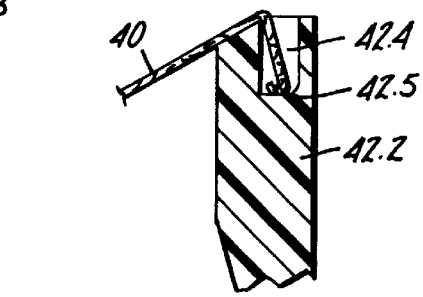
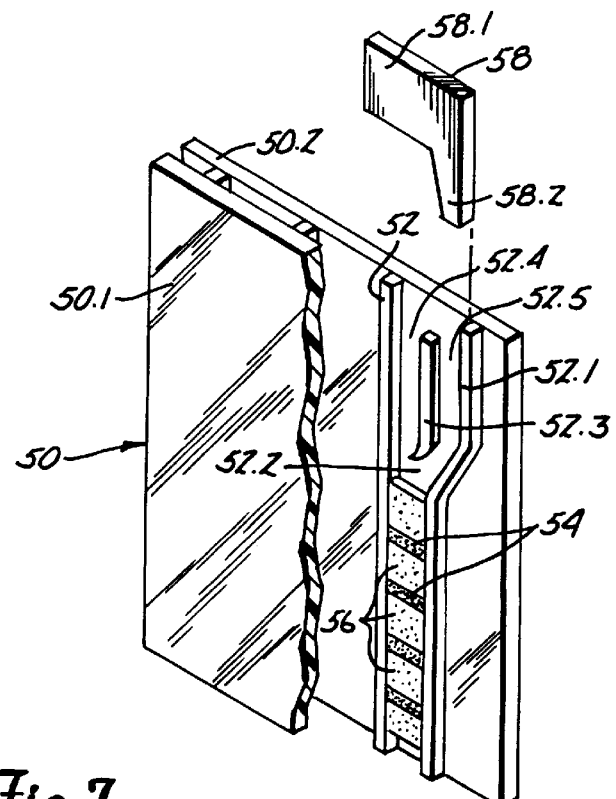

CHEMICAL ANALYSIS APPARATUS AND METHOD

This is a continuation of Ser. No. 574,607 now abandoned, filed Aug. 28, 1990, which is a divisional of Ser. No. 467,229, filed Feb. 23, 1983, now U.S. Pat. No. 5,073,484, which is a continuation in part of Ser. No. 356,459, filed Mar. 9, 1982, abandoned.

FIELD OF THE INVENTION

The invention is in the field of quantitative chemical analysis, and is particularly useful in the detection and analysis of small amounts of chemical substance in such biological fluids as milk, blood, urine, etc.

DESCRIPTION OF THE PRIOR ART

Procedures for quantitatively determining the concentration of chemical substances in solutions are legion. Many of these procedures are long and tedious, and are highly susceptible to human error. Many procedures involve the reaction of the chemical moiety—the analyte—to be detected with a reactant to form a product, the procedures including a step of determining the amount of reactant that is consumed (e.g., as in titrations), or the amount of product that is produced (e.g., as by measuring the absorption of light by the product of a chromogenic reaction), or as by measuring the amount of the chemical moiety or reaction product that can be separated from the solution (e.g., by distillation), etc. Some quantitative analysis procedures, such as are used in radioimmuno-assays, involve competitive reactions between labeled analytes (e.g., labeled with radioisotopes of iodine, enzymes, or fluorescent, chromogenic or fluorogenic molecules) in known quantities and unknown amounts of unlabeled analytes, the amount of analyte in the unknown solution being related to the measured radioactivity or other property of a specimen resulting from the test after suitably separating the reacted or bound analyte from the unreacted or unbound analyte, or through properties of the bound and unbound labeled analyte that permit them to be distinguished. Many of such procedures involve changes in color (as when chemical indicators are employed that respond by color changes to differences in hydrogen ion concentration), or in turbidity (as when the procedure involves the formation of a solid reaction product).

Certain analyses involve the passage of a fluid, such as air, through a column containing a reactant which may change color upon contact with an ingredient of the air. For example, U.S. Pat. No. 3,286,506 describes a gas analyzing technique in which a measured amount of gas is passed through a glass cartridge containing an indicator, the amount of gas to be detected being proportional to the amount of indicator within the column that changes color. Similar devices are shown in U.S. Pat. Nos. 3,312,527 and 3,545,930.

There is a recurring trend in the field to provide analytical procedures which are characterized by speed, simplicity, and by a reduction in the vulnerability of such procedures to human error. Simple, rapid tests, for example, have been marketed for determining the approximate level of blood sugar for diabetics. Such tests, however, often are relatively imprecise. It would be highly desirable to provide a quantitative test for chemical moieties that on the one hand would be characterized by high sensitivity and that yet on the other hand would be characterized by simplicity, rapidity and relative freedom from human error.

SUMMARY OF THE INVENTION

In one embodiment, the invention provides an apparatus for the quantitative analysis of a chemically reactive substance (hereafter referred to as an "analyte"), in a carrier fluid such as a liquid. The apparatus includes a fluid-permeable solid medium that has a predetermined number of successive, spaced reaction zones and which defines a path for fluid flow sequentially through such zones. "Fluid" herein is typified as a liquid. Predetermined quantities of a reactant are bound to the solid medium in such zones and are capable of reaction with the analyte or with an analyte derivative, to result in the formation of a predetermined product. The apparatus may further include detector means for detecting, in the spaced zones, the presence of the analyte or its derivative, the reactant, or the predetermined product resulting from the reaction between the analyte or its derivative and the reactant. In addition, the apparatus may include means for suppressing the detectability of trace amounts of the analyte or its derivative, the reactant, or the predetermined product resulting from the reaction between the analyte or its derivative and the reactant.

As used herein, the terms "reactant", "reactive" and the like when used in connection with the reaction between the analyte or its derivative and the reactant refers to the ability of the reactant to react, by covalent or hydrogen bonding or by any other means, with the analyte or its derivative to form or result in the formation of a predetermined product. That is, such terms are used in their broadest sense as referring to the ability of the reactant to in any way act upon, be acted upon, or interact with the analyte or analyte derivative in a manner that detectably alters the analyte or its derivative, the reactant or both to thereby result in the formation of a reaction product. Similarly, "reaction product" means any product resulting from the reaction of the analyte or its derivative and the reactant and that is detectably different from both. "Analyte derivative" means a chemical moiety derived from an analyte, and desirably is a tagged or labeled form of the analyte as may be employed in analytical procedures involving competing reactions between an analyte and its tagged or labeled derivative.

In the apparatus of the invention, the reactant is bound to the permeable solid medium in the successive, spaced zones through which the analyte passes. A procedure employing the apparatus may take the form in which the analyte or its derivative, as it passes through the reaction zones, becomes bound to the reactant and the presence of the analyte or its derivative within the reaction zones is detected, as by color change or the like. Similarly, in a slightly modified embodiment, the analyte or its derivative may react with the reactant to result in the formation of a product that itself remains bound in the reaction zones, and the product itself is then detected. In these embodiments, one may determine with considerable precision the concentration of the analyte by detecting how many of the successive reaction zones, beginning with the upstream zone, show the presence of the analyte or its derivative, or of the product resulting from the reaction between the reactant and the analyte or analyte derivative. In another embodiment, the reactant that is bound to the permeable solid medium may itself be capable of detection by suitable detection means and may be disabled from such detection when reacted with an analyte or analyte derivative. In this manner, as the analyte or analyte-analyte derivative composition passes through successive reaction zones, the reactant in the successive zones is disabled from such detection until substantially all of the analyte or analyte-analyte derivative composition has been exhausted, while remaining downstream reaction zones still contain reactant that can be detected. In a modified form, the reaction between the analyte or analyte derivative and the reactant may cause the latter to become unbound from the solid medium to which it was attached and hence be washed from the successive zones. When the analyte or analyte derivative or both has thus been exhausted, subsequent or downstream reaction will display reactant that is yet bound to the permeable medium and which can be detected. In such embodiments, one may count the number of zones in which the reactant has been disabled beginning with the upstream zone.

As used herein, "analyte" refers not only to the particular chemical moiety for which analysis is desired, but also to chemical moieties that are reaction products of the moiety to be determined with another chemical moiety. For example, a biological fluid containing an unknown amount of a chemical moiety may be reacted in solution or otherwise with another chemical moiety to provide a product, the concentration of which is related to the initial concentration of the chemical moiety to be measured. The resulting product, then, may become the "analyte" for use in the apparatus and method of the invention. Accordingly, "analyte" refers to any chemical moiety which is to be measured quantitatively.

In a preferred embodiment, the invention employs immunochemical reactions in which the analyte and the reactant represent different parts of a specific ligand-antibody (antiligand) binding pair.

DESCRIPTION OF THE DRAWINGS

FIG. 4 is a plan view of another embodiment of an apparatus of the invention;

FIG. 5 is a perspective view of yet another test apparatus of the invention;

FIG. 6 is a broken-away cross sectional view taken along line 6—6 of FIG. 5; and FIG. 7 is a perspective, broken-away view of another test apparatus of the invention.

DETAILED DESCRIPTION

Figure 1:
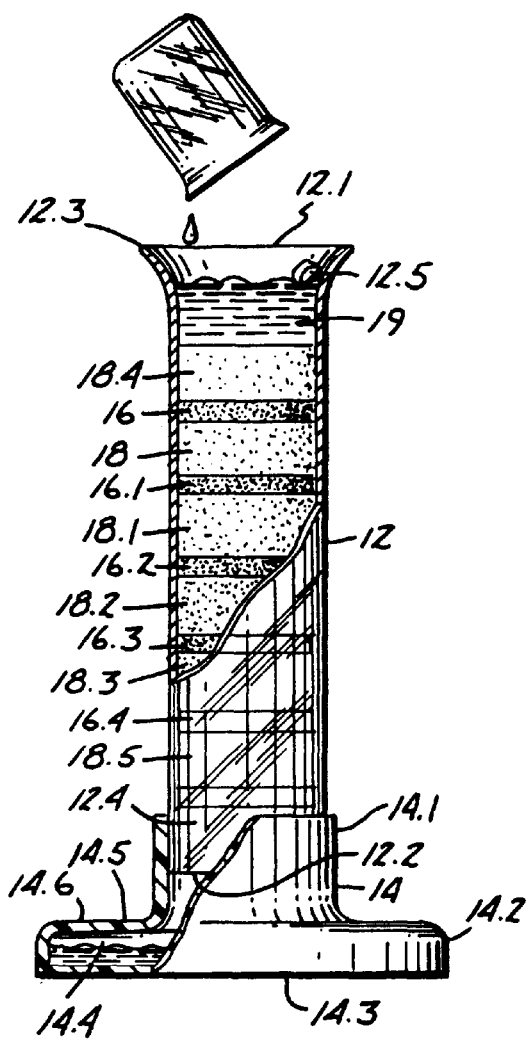
FIG. 1 is a broken-away view, in partial cross-section, showing an apparatus of the invention.

With reference to FIG. 1, a transparent, hollow column of glass or the like is designated 12 and has open top and bottom ends (12.1, 12.2). The top end (12.1) preferably is flared outwardly as shown at (12.3). A standard (14) is provided at the bottom end of the column, and may have a hollow, upstanding portion (14.1) into which the bottom portion (12.4) of the column may be snugly fitted as by a press fit. The standard includes a relatively wide bottom portion (14.2) having a flat, horizontal surface such as a table. The interior (14.4) of the standard preferably is hollow, and an upper wall (14.5) of the standard preferably is provided with a breathing aperture (14.6) so as to permit air to escape from the column when liquid is poured into the upper end (12.1) of the column. The aperture (14.6) may, if desired, be fitted with a loose, porous plug, such as a cotton plug, to retard leakage from the device when it has been disposed of in a trash container or the like. It may also, if desired, be fitted with a flexible tubing which may connect it with a pump (e.g., peristaltic, syringe drive withdrawal, etc.) typifying flow control means to control the flow rate of the liquid through the assay column.

Within the column are positioned successive, spaced reaction zones (16, 16.1, 16.2, 16.3, etc.), occupied by a permeable solid medium such as beaded agarose, beaded polyacrylamide, porous glass, cellulose or other materials permeable to liquid and compatible with the analyte, analyte derivatives reactant and detector means. To the medium in the reaction zones is bound a reactant, as will be described more fully below. The interior of the column, as will now be understood, describes a generally vertical liquid flow path, and the permeable solid medium positioned in the reaction zones desirably occupies the entire cross-section of the flow path. Between the spaced reaction zones are positioned preferably nonreactive spacer layers (18, 18.1, 18.2, 18.3 and so on) of a liquid-permeable solid medium through which liquid may flow, the spacer layers preferably being in intimate contact with the reaction zones. The spacer layers desirably are of the same permeable solid medium as the reaction zones, and, preferably, spacer layers 18.4, 18.5 are provided at the top and bottom of the columns as well so that each reaction zone is sandwiched between spacer layers. At its upper end, the column (12) may be provided with an aperture (12.5) spaced a given distance above the spacer layer (18.4) so as to provide a predetermined volume between the aperture and top surface of the spacer layer. In a known manner, as a liquid (represented as (19) in the drawing) is poured into the open upper end (12.1) of the column, it will occupy the open volume at the top of the column and any amount of the liquid (20) in excess of that desired may escape outwardly through the aperture (12.5), thereby insuring that no more than a given, predetermined amount of the liquid passes downwardly in the column. The space (20) may, if desired, be filled or partially filled with a porous, nonreactive material such as glass wool or similar material to avoid splashing of the liquid within the upper end of the column.

To the liquid-permeable solid medium within the spaced reaction zones (16, 16.1, etc.) is bound a reactant that is reactive with a given analyte or analyte derivative to form a product, all in accordance with the above definitions and as exemplified herein. As a typical example, the reactant and analyte may be so chosen that the analyte or its derivative becomes chemically attached to the reactant as the solution (20) of analyte or analyte and analyte derivative solution (the "test solution") passes downwardly through the column, care being taken that the total amount of reactant within the column is in excess of that required to so react with the expected quantity of analyte and analyte derivative in the solution. After the test solution has begun its passage downwardly through the column, a wash solution, typically distilled and deionized water, optionally may be poured into the open end of the column to further aid the downward passage of the test solution through the column. Finally, an indicator or detector material that detects the presence of analyte or analyte derivative, reaction product or reactant, as by causing a color change within the zones (16, 16.1 and so on) may be poured into the upper end of the column. As the test solution flows downwardly through the column, predetermined amounts of the analyte or its derivative are reacted with or bound to the reactant in each such layer until the analyte or its derivative have been exhausted from the solution. The concentration of analyte in the solution can be determined by merely counting the number of successive zones, beginning at the top of the column, that have changed color. In another emobidment, the reactant that is bound to the medium in the zones (16, 16.1 and so on) may be deactivated or disenabled by reaction with the analyte or analyte derivative or both, and the detector which is employed may determine, as by a color change, the presence of nondisabled reactant. In this embodiment, the reactant in successive zones contacted by the test solution will be disabled until analyte and analyte derivative have been exhausted from the solution. Upon detecting which of the reaction zones contain reactant that has not been disabled, one may determine the concentration of analyte in the solution by counting the number of zones beginning at the top of the column in which reactant is not detected. Of course, in this embodiment as in the embodiment set out above, one may also count the number of zones beginning with the bottom of the column as well.

Figure 2:
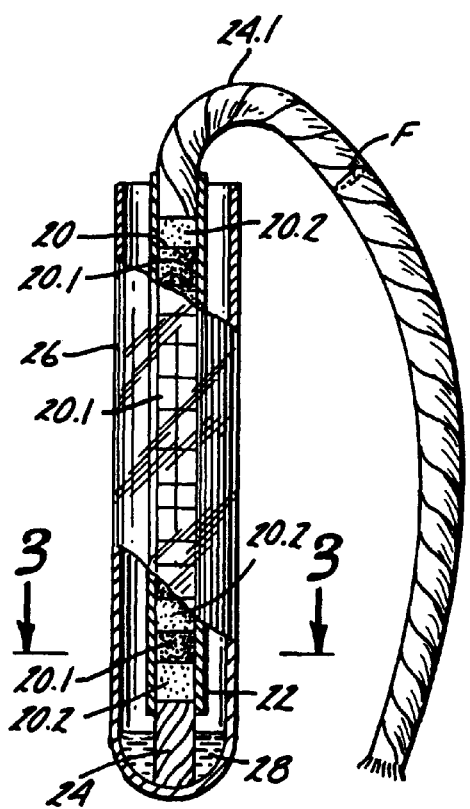
FIG. 2 is a broken-away view, in partial cross-section, showing another apparatus of the invention.
Figure 3:
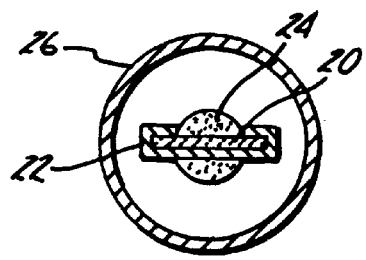
FIG. 3 is a cross-sectional view taken along line 3—3 of FIG. 2.

Another physical embodiment of the apparatus of the invention is shown in FIGS. 2 and 3 in which "wicking", or upward capillary flow of a liquid through a strip of filter paper or similar material is employed, the strip having successive, spaced reaction zones. In this embodiment, the permeable solid medium may take the form of a strip of filter paper, which is designated generally as (20) in FIGS. 2 and 3. Within spaced zones (20.1) of the filter paper strip is bound a reactant, as above-described, the spaced zones being separated by spacer layers or sections (20.2). One method of preparing the strip (20) involves binding a reactant to small, individual rectangular paper filter pieces, and then alternating these pieces, which form the reaction zones, with similar pieces of filter paper that do not contain the reactant, the alternating pieces of filter paper being held together, for example, by a thin strip of adhesive tape. Other, more sophisticated methods of manufacture will be apparent to those skilled in the art.

As shown in FIGS. 2 and 3, the strip (20) of filter paper may be positioned in an elongated plastic holder (22) having a generally C-shaped cross-section. The bottom of the holder is adapted to receive the end of a wick (24) which may consist of twisted strands of cotton or other fibrous material. A similar wick (24.1) is received in the upper end of the plastic holder. The ends of the wicks (24, 24.1) contact the ends of the filter strip (20). As shown in FIG. 2, the upper and lower sections of the filter paper strip which come into contact with the wicks (24, 24.1), are spacer layers (20.2) so that each reaction zone (20.1) is sandwiched between spacer layers (20.2). The filter paper strip and holder are adapted for insertion into a test tube (26) or other container so that the lower wick (24) contacts the bottom of the test tube and the upper wick (24.1) extends out of the test tube and then downwardly toward its bottom, all as shown in FIG. 2. A test solution (28) placed in the bottom of the test tube (26) is thus caused to flow by capillary action upwardly through the length of the filter paper strip, successively contacting the reaction zones (20.1) in a manner analogous to the flow of test solution through the column depicted in FIG. 1. As will be described more fully below, the filter paper strip and holder can be moved from one test tube to another so that different solutions can be caused to sequentially flow through its length.

Referring now to FIG. 4, an apparatus of the invention is embodied in a disc of permeable, solid medium such as filter paper, porous glass, etc. (30). The disc (30) may be placed horizontally in a suitable container such as a petri dish. At its center, the disc (30) is provided with a well (30.1) to receive a test solution or other solution. Reaction zones, spaced radially from the well (30.1), are shown as annular rings (30.2), and are separated from one another by spacer layers also in the form of annular rings (30.3). Spacer layers preferably form the innermost and outermost rings of the disc. The reaction zones (30.2) and the spacer layers (30.3) are concentric. Test solution that is admitted to the central well (30.1) is thus carried radially outwardly of the well by capillary action or by diffusion, aided by centrifugal force if desired, the test solution successively passing through the spaced reaction zones (30.2).

FIGS. 5 and 6 show another embodiment of a device of the invention. The device includes a filter paper strip (40) similar to that of FIGS. 2 and 3 and containing spaced reaction zones (40.1) separated by spacer layers (40.2). A holder, preferably of plastic, is designated (42) and has a flat base (42.1) with upwardly extending legs (42.2, 42.3) carried at its ends. The leg (42.2) is provided with an upwardly open well (42.4) into which may be inserted the upper end of the filter paper strip (40), care being taken that the end (42.5) of the filter paper extends downwardly to the floor of the well. The strip of filter paper extends obliquely downwardly from the well, and its lower end is captured in a slot (42.6) formed in the leg (42.3). In use, the test solution or other solution is placed in the well (42.4), and is carried downwardly of the strip by both gravity and capillary action, the solution sequentially encountering the spaced reaction zones (40.1).

FIG. 7 shows yet another embodiment of a device of the invention which can be used for multiple concurrent tests. The device, designated (50), includes a pair of spaced plates (50.1, 50.2). Referring to the right-hand portion of FIG. 7, the space between the plates is divided into generally vertical channels by means of elongated spacers (52, 52.1). As shown in the drawing, the channel (52.2) formed by the spacers has a wide upper section and a narrow lower section. The lower section is provided with a series of vertically spaced reaction zones (54) comprising a liquid-permeable solid medium to which is bound a reactant, the medium being any of those described above. Between the reaction zones, are placed spacer layers (56), the spacer layers sandwiching between them the reaction zones (54). Between the spacers (52, 52.1), at the upper end of the channel is placed an elongated vertical divider (52.3) which divides the upper portion of the channel into two sections (52.4) and (52.5). A plug (58), which may be made of the same material as the spacers, has an upper, finger-gripping portion (58.1) and a lower, tapering plug portion (58.2) adapted to be inserted in the channel (52.5). The flat surfaces of each of the spacers and plug, of course, contact the facing surfaces of both glass plates to prevent leakage of material from the channels.

In use, a solution such as a test solution is poured into the upper end of the channels formed by the spacers (52, 52.1), and the plug (58) is then inserted to provide an air-tight upper seal in the one channel (52.5). As a result, liquid in the other channel (52.4) preferentially flows downwardly through the reaction zones and spacer layers. When the liquid level in the channel (52.4) falls below the lower end of the spacer (52.3), air can bubble upwardly through the channel (52.5), permitting the contents of that channel to empty downwardly through the reaction zones as well. In this manner, the sequential flow of liquid, first from channel (52.4) and then from channel (52.5), is rendered automatic. Preferably, one of the plates (e.g., plate 50.1) is transparent so that the results of any color change in the reaction zones may readily be observed. The other plate (50.2) may be transparent or may be of an opaque white or other light color to serve as a background against which color changes can readily be seen.

ANALYTES-REACTANTS

Analytes that can be detected in accordance with the present invention include substantially all chemical substances that are reactive with a reactant to form a product, as above discussed. It will be understood that the invention is not limited to any particular analyte or reactant, but is useful for substantially any analyte-reactant combination.

Many analytes may be analyzed simply by adapting known chemical reactions to the invention.

For example, carbon dioxide may be analyzed with phenolphthalein at a slightly alkaline pH. Calcium ion may be analyzed utilizing a reactant comprising calmodulin and mammalian phosphodiesterase or another calmodulin-sensitive enzyme (Maekawa and Abe, *Biochemical and Biophysical Research Communications* 97:621 (1980)). Ferrous ion may be analyzed utilizing, as a reactant, a ferrocene derivative (Katz, et al, J. Am. Chem. Soc. 104:346 (1982)). A large number of additional examples may be selected from the list of organic analytical reagents compiled by John H. Yoe in *Handbook of Chemistry and Physics*, p.D 126–129, 57th Edition, Robert C. Weast, Ed., CRC Press, Cleveland, 1976, and in other references cited therein.

Typical analyte-reactant pairs selected from the field of organic chemistry similarly may be chosen by adapting known chemical reactions to the invention. For example, almost any phenol may be analyzed with Gibbs Reagent (2,6-dichloro-p-benzoquinone-4-chlorimine) (Dacre, J., *Analytical Chemistry* 43:589 (1971)). A reagent for Indoles is p-dimethylaminobenzaldehyde (Fieser and Fieser, *Reagents For Organic Synthesis*, Volume 1, p.273, John Wiley & Sons, Inc., New York, (1967). The last-mentioned reference also shows the use of phenylhydrazine as a reactant for cortisone and similar steroids, and the use of sulfoacetic acid as a reactant in the Liebermann-Burchard test for unsaturated sterols. Amino acids and ammonium salts may be analyzed using the reagent ninhydrin (indane-1,2,3-trione hydrate) (Pasto, et al *Organic Structure Determination*, p.429, Prentice-Hall, Inc., Englewood Cliffs, N.J., 1969). Reducing sugar may be measured with Red Tetrazolium (2,3,5-triphenyl -2H-tetrazolium Chloride) (Fieser, *Organic Experiments*, p.135, Raytheon Education Co., Lexington, Mass., 1968).

Various other analyte reagent pairs may be selected from the field of chemistry for adaptation to the invention from such reference works as: Schuurs, et al, U.S. Pat. No. 3,654,090 (Enzyme-Linked Immunosorbent Assay); Kay, U.S. Pat. No. 3,789,116 (Fluorescent Labeled Antibody Reagents); Rubenstein, et al, U.S. Pat. No. 3,817,837 (Homogeneous Enzyme Immunoassay); Ling, U.S. Pat. No. 3,867,517 (Radioimmunoassay); Giaever, U.S. Pat. No. 3,906,490 (Radial Immunodiffusion); Ullman, U.S. Pat. No. 3,996,345 (Flourescence Quenching Homogenous Immunoassay); Maggio, U.S. Pat. No. 4,233,402 (Enzyme Channeling Homogeneous Enzyme Immunoassay); Boguslaski, et al, Canadian Patent 1,082,577 (Hapten-Cofactor Homogeneous Enzyme Immunoassay); Schonfeld, H., Ed., "New Developments in Immunoassays", *Antibiotics and Chemotherapy*, Volume 26, 1979; O'Sullivan, et al, "Enzyme Immunoassays: A Review", *Annals of Clinical Biochemistry* 16:221 (1979); Schuurs, et al, *Enzyme Immunoassay*, Clin. Chim. Acta. 81:1 (1977); Feldmann, et al, Eds., *First International Symposium On Immunoenzymatic Techniques*, INSERM Symp. No. 2, North Holland Publishing Co., Amsterdam, 1976; Williams, et al, *Methods in Immunology and Immunochemistry*, Volume 3, Academic Press, New York, 1971; and Yalow, et al, J. Clin. Invest. 39:1157 (1960).

Yet other analyte-reactant pairs may be found in: reference works such as Feigl, F., *Spot Tests in Inorganic Analysis*, 6th edition, Elsevier Publishing Co., New York, 1972; Feigl, Fritz, *Spot Tests in Organic Analysis*, 7th edition, Elsevier Publishing Co., New York, 1966; Snell, F. and Snell, C., *Colorimetric Methods of Analysis*, Vols. 1–4AAA, Van Nostrand Reinhold Co., New York, 1967–74; and Braibanti, A., Ed. *Bioeneretics and Thermodynamics: Model Systems—Synthetic and Natural Chelates and Macrocycles as Models for Biological and Pharmaceutical Studies*, D. Reidel Publishing Co., Boston, 1980.

The references identified above are incorporated herein by reference.

Of particular importance to the instant invention are those analyte-reactant combinations that form specific binding pairs of which one is an antibody and in which the other is a ligand to which the antibody is specific.

Such immunochemical reactant pairs are well-known in the art, and a wide variety of tests have been devised to detect the presence or quantity or both of an analyte, particularly when the analyte is present only in exceedingly small concentrations. Reference is made to the above-identified patents and publications.

DETECTORS

The detectors useful in the invention are capable of detecting the presence in the successive reaction zones, of analyte, analyte derivatives, reactants, or the predetermined reaction product, all as described above. The means of detection may take various forms. In the preferred embodiment, detection is signaled by a change of color, or a lack of a change of color, in the respective reaction zones of the apparatus. However, detection may be signaled by other means as well, such as by luminescence or fluorescence of the zones, radioactivity of the zones, etc. For many reactions, detection is signaled by a change in pH, and the detector may hence take the form of a pH color indicator such as phenolphthalein, Nile Blue A, Thymol Blue, and Methyl Violet. In other tests, one may detect the presence or absence of the appropriate chemical moiety in a reaction zone by observing whether a solid reaction product has settled upon the succeeding spacer layer. Various detector mechanisms are known to the art, and need not be described in detail. In the preferred embodiment, however, which makes use of immunochemical reaction between the analyte or the analyte and its derivative and the reactant, often very small concentrations of analyte are to be measured and accordingly a magnifying or amplifying mechanism may suitably be employed. One such mechanism makes use of enzymes to promote the reaction of a reaction product with a detector moiety to in turn provide a visual color indication. For example, the analyte to be tested may be provided in admixture with a known quantity of an analyte-glucose oxidase conjugate as an analyte derivative, the spaced, sequential reaction zones of the apparatus containing an antibody specific to the analyte. A signal generating system, such as horseradish peroxidase bound to the antibody in the permeable solid medium in such zones and a chromogenic material such as o-dianisidine (added, with glucose, to the test solution) can be employed. The addition of the test solution, containing the analyte, the analyte-glucose oxidase conjugate, glucose, catalase and o-dianisidine, is then flowed through the apparatus, such as the column depicted in FIG. 1. The analyte and the analyte-glucose oxidase conjugate compete for binding sites on the bound antibody, thereby resulting in a color formation due to the reaction of the o-dianisidine with hydrogen peroxide produced by the glucose oxidase—catalyzed reaction of oxygen with glucose. Unreacted analyte and analyte-glucose oxidase conjugate flow to successive zones until the admixture has been exhausted of analyte and analyte-glucose oxidase conjugate. A variety of modifications of this procedure, of course, are known to the art.

EXAMPLE I

The chromogen 5,5' [3-(2-Pyridyl)-1,2,4-triazine-5,6-diyl]bis-2-furansulfonic acid, disodium salt, ("Ferene", a trademarked product of Chemical Dynamics Corp.) is used for the determination of serum iron in soluble assays through measurement of the absorbance at 593 nm, at which wavelength any interference from other pigments in the serum should be minimized. It may be covalently coupled to useful carrier derivatives through nitration, reduction, diazotization and diazonium coupling to proteins (such as albumin) immobilized on agarose beads, paper strips or other suitable permeable solid medium. This immobilized signal-generating reagent (chromogenic chelating agent) is physically arranged in sequential spaced layers or bands (reaction zones) through which the test fluid will migrate.

Small columns are prepared from silanized Pasteur pipettes by breaking off both ends, attaching a short piece of tubing to the bottom (constricted) end and inserting glass wool plugs in the tube bottoms. The columns are packed by sequential insertion of layers of agarose-Ferene separated by layers of unmodified agarose. Typically, 0.4 ml of a 1:1 agarose suspension is applied directly above the support, followed by alternating layers of 50 microliters of a 1:1 suspension of agarose-Ferene and 0.2 ml of agarose suspension. After each addition to the column, the walls of the columns are rinsed with phosphate-buffered saline (PBS) and the solution above the gel is allowed to flow into the gel before addition of the next layer.

For use in the assay, the tubing at the bottom of the prepared column is connected to a peristaltic pump to control the flow rate of the assay. An appropriate dilution of test sample for iron analysis is applied to the column. The iron solution ("test" solution) is passed through the assay column at controlled flow rates, typically between 10 and 15 minutes for complete entrance. When all the solution is into the gel bed, the columns are rinsed with water. As the test solution flows through, color develops in some of the Ferene-containing reaction zones. The number of colored zones resulting is a function of the concentration of iron in the test solution.

EXAMPLE II

A. The enzyme cholinesterase reacts with and is inhibited by toxic organophosphate and carbamate agents. Cholinesterase and the chromogenic sulfhydryl reagent 5,5'-Dithiobis-(2-nitrobenzoic acid) (Ellman's Reagent) are immobilized upon agarose beads, which are then assembled into columns according to Example I. A test solution (diluted blood serum) is added to the column and migrates through the reaction zones following which a solution of butyryl-thiocholine iodide is added. The zones retaining catalytically active cholinesterase will generate a yellow color through reaction of the thiocholine produced by the hydrolytic activity of the cholinesterase, with the immobilized Ellman's Reagent. The presence of reactive cholinesterase-inhibiting toxin in the test sample will result in fewer colored bands, which will be in the downstream end region of the column.

B. Amino acids and other nucleophilic amine compounds are measured by use of the chromogenic reagent 2,4-dinitrofluorobenzene (FDNB), which produces a yellow product upon reaction. A 0.1 ml aqueous sample, containing about 0.1–1.0 micromoles of amino analyte, is transferred to a siliconed glass vessel. The pH is adjusted to 7.0, if necessary, and two milligrams (25 micromoles) of $NaHCO_3$ is added and dissolved. Next is added 0.12 ml of 0.15% FDNB in absolute alcohol (1.5 micromoles). This solution is prepared fresh shortly before use. After the reaction has neared completion, it is analyzed for remaining FDNB (reactant) content by flow exposure to the assay system prepared according to Example I. In this case, a similar amine-containing analyte is immobilized in the zones in a permeable solid medium at a known content (e.g., 0.1–0.25 micromoles per reaction zone). After rinsing with 50% ethanol in aqueous solution, the number of yellow reaction zones produced and remaining after rinse will be inversely related to the amount of analyte in the test sample.

EXAMPLE III

The IgG fraction from rabbit anti-penicilloylbovine gamma globulin was partially purified by precipitation with 33% saturated ammonium sulfate. The precipitate was redissolved and dialyzed against phosphate buffered saline (PBS). This IgG preparation was used for immobilizing antibodies onto beaded agarose. The agarose was suspended in dioxane, then reacted with carbonyldiimidazole. After being washed with dioxane, it was suspended in water, and then in aqueous borate buffer, pH 9.0. The IgG was then added to the activated agarose and the gel suspension stirred by rocking at 4° C. for 2 days. After extensive washing with PBS, the gel containing immobilized antibody was ready for use in the assay.

Small columns were prepared from silanized Pasteur pipettes by breaking off both ends, attaching short pieces of tubing to the bottom (constricted) ends and inserting glass wool plugs in the column bottoms. The columns were packed by sequentially inserting alternating layers of agarose-IgG separated by layers of unmodified agarose. Typically 0.4 ml of 1:1 agarose suspension was applied directly above the plugs, followed by alternating layers of 50 microliters of a 1:1 suspension of agarose-IgG (to form the reaction zones) and 0.2 ml of agarose suspension (to form spacer layers). After each addition, the walls of the columns were rinsed with PBS and the solution above the gel was allowed to flow into the gel before addition of the next layer.

For use in an assay, tubing at the bottom of the prepared column was connected to a peristaltic pump to control the flow rate of the assay. An appropriate dilution of penicilloyl-glucose oxidase ("Pen-GO") (typically 0.1 microgram Pen-GO in 1 ml PBS) with or without known amounts of the analyte (penicilloyl-epsilon amino caproate) (Pen-EAC), was applied to the column. The Pen-GO was prepared by reacting penicillin G with glucose oxidase in borate buffer, pH 9.0, for 2–3 days at 4° C. The Pen-GO solution was passed through the assay column at controlled flow rates, typically between 10 and 15 minutes for complete entrance into the gel. When all the solution was into the gel bed, a detector solution was added to the column. The detector solution was prepared as follows: 0.20 ml of horseradish peroxidase (HRP) solution (2 mg/ml), 2 ml of 18% glucose solution, 1 ml of 0.2 M phosphate buffer (pH 6.0) and 0.100 ml of 1% o-dianisidine was diluted 1:10 in PBS and 1 ml or less was applied to the columns at the same flow rate as the previous solutions. Brown color developed in some of the reaction zones. Presence of the penicilloyl moiety in the Pen-Go solution results in the upper reactive zone or zones being lighter in color, with color being generated in zones further down the column.

This Example may be repeated for the analysis of serum albumin (a large protein molecule) by replacement of the penicillin-glucose oxidase conjugate with an albumin-glucose oxidase conjugate.

EXAMPLE IIIA

Peroxidase-labeled IgG prepared from rabbit antiserum against penicillin was immobilized in small strips of filter paper by the method reported in Example III. Catalase was bound to other, similar strips of filter paper. The first and second mentioned strips were then cut into rectangular shapes to provide, respectively, reaction zones and spacer layers. The small rectangular pieces of filter paper were then layed onto a strip of adhesive tape, alternating the reaction zones and spacer layers with edges of the sequential pieces of paper overlapping or at least touching one another to provide a continuous capillary flow path.

Penicilloyl-glucose oxidase ("Pen-GO") in a solution of Human Serum Albumin ("ESA") was freeze-dried inside a test tube. Within another test tube, made of brown glass for protecting the contents from light, was freeze-dried a solution of o-dianisidine and glucose in phosphate-buffered saline at pH 6.0.

A short wick was attached to the bottom of the prepared filter paper strip described above, and a longer wick was placed in contact with the upper end of the strip. The strips themselves can be stored under refrigeration, and preferably are retained in a wet condition resulting from the preparation described above.

In one example of use, a test solution consisting of a measured volume of milk containing a known concentration of penicillin G is added to the test tube containing the freeze-dried Pen-GO, and the tube is shaken gently to mix the contents. The filter paper strip is then inserted into the tube with its upper, longer wick extending over the lip of the tube and then downwardly as shown in FIG. 2. When the entire solution has been taken up by the strip (or, alternatively, when the solution reaches an arbitrary flow line marked on the upper wick and designated "F" in FIG. 2) the filter paper strip is removed from the test tube and is placed in the brown glass tube to which previously has been added water to dissolve the freeze-dried contents thereof. The latter solution similarly wicks upwardly through the filter paper strip, causing color development to occur in certain of the reaction zones as determined by the quantity of penicillin G in the initial test solution.

In this example, the penicillin G in the milk and the penicillin of the Pen-GO compete for binding sites on the antibodies immobilized in the reaction zones of the filter paper strip. Of course, larger concentrations of penicillin G in the milk sample cause the penicillin G and the Pen-GO to migrate further through the filter paper strip. The presence of Pen-GO in any of the zones is indicated through the development of color from the reaction of $H_2O_2$ with o-dianisidine, the $H_2O_2$ being formed from the glucose oxidase in the presence of glucose and oxygen, and as catalyzed by the peroxidase. The catalase in the spacer layers catalyzes the conversion of $H_2O_2$ into $O_2$ and $H_2O$, and thus prevents migration of $H_2O_2$ from one reactive zone to another.

As with each of the apparatuses described herein, the device of this example may be calibrated by determining how many of the reaction zones become colored as a result of the test procedure. For example, one of the reaction zones may change color only when the test solution (e.g., milk) contains at least 9 nanograms of analyte (e.g., penicillin G) per ml. For a sample of milk containing an unknown concentration of penicillin G, one merely counts the number of reaction zones that have changed color to find the narrow, defined concentration range within which lies the penicillin G concentration.

EXAMPLE IV

Antibody against a polyvalent antigen (e.g., serum albumin) analyte is labeled with peroxidase and bound to permeable solid medium according to Example III to form reaction zones in a column. Another batch of the same or similar antibody is labeled with an enzyme such as glucose oxidase. Into the column is poured a test sample containing an unknown amount of analyte antigen. Through the column is then flowed the soluble glucose oxidase-antibody in the presence of glucose plus catalase plus o-dianisidine. The number of colored bands resulting is directly related to the amount of analyte antigen in the test sample relative to the antigen binding capacity of the antibody zones. In this example, the antigen first reacts with the bound antibody and binds to the antibody, forming a predetermined product. The latter, in turn, is detected by the coupling of the glucose oxidase antibody conjugate to available antigenic sites on the antigen followed by the color forming reaction.

EXAMPLE V

An analyte or a derivative thereof (e.g., penicillin-peroxidase) is covalently bound to a permeable solid medium according to Example III. An enzyme-labeled receptor (e.g., glucose oxidase-antibody against penicillin) is prepared and exposed to the immobilized analyte to form the specific binding complex (e.g., immune complex). The assay unit is assembled according to Example III. Subsequent exposure to a test sample containing an unknown amount of analyte is done at elevated temperature (e.g., 60° C.) to hasten the attainment of equilibrium through competitive binding of the immobilized analyte and analyte in the test sample with the enzyme-labeled antibody. Analyte in the test sample under such conditions will competitively displace the labeled antibody from the immobilized analyte. The number of colored reaction zones resulting from the procedure is inversely related to the amount of analyte in the test sample. These bands will appear in the terminal or downstream portion of the column.

EXAMPLE VI

Three assay columns with 4 reaction zones each were prepared according to Example III, except that the top reaction zone was prepared with 75 microliters of IgG-agarose suspension (1:1) and the lower 3 zones with 50 microliters. Test samples containing 0, 50 and 200 nanograms Pen-EAC, were placed in different columns, with each test sample containing 200 ng Pen-GO per ml. Flow time for sample application was 20 min. Application of the solution of signal generating reagents produced 2 colored zones with the 0 ng Pen-EAC sample, 3 in the 50 and 4 with the 200 ng sample.

A wider and more precise range of analyte content, of course, may be measured by using a larger number of assay zones.

In a preferred embodiment, only a single pass through the apparatus of a single liquid material is required. An analyte may be mixed with an analyte derivative, chromogen or other material and flowed through the apparatus to yield an appropriate test result. In a further preferred embodiment, the apparatus is chemically complete in that it includes all reactants and other chemicals necessary or desirable for the quantitative analysis of an analyte; that is, all that is required is that the analyte in a liquid carrier be flowed through the apparatus. Elements of the apparatus that, if combined, would undergo reaction in the absence of the analyte may be maintained in different zones. For example, the bottom-most layer (20.2) of the strip of FIG. 2 may contain a reactant physically separated from reactants in the adjacent reaction zone. When the analyte in a carrier liquid is flowed through the layer (20.2), the reactant in this layer together with the analyte and carrier liquid is flowed into the first reaction zone. If desired, a reactant may be provided in the form of a solid and may merely be placed upon the upper layer (18.4) of the column of FIG. 1, the reactant being dissolved by and carried with the liquid carrier and analyte into the column.

The above-described embodiments are typified by the following Examples VII–IX which also describe and exemplify a preferred format of the invention.

This format requires at least two enzymes, one of which is coupled to an analyte to form an analyte derivative and catalyzes a color-forming reaction, and another enzyme that is immobilized in reaction zones which also contain antibody to the analyte, the latter enzyme providing substrate for the color-generating enzyme. In this format, therefore, only a single solution which consists of or contains the analyte test sample is flowed into or through the solid medium after which color develops in the reaction zones, the number of colored zones being directly related to the concentration of analyte in the test sample.

EXAMPLE VII

The IgG fraction from rabbit anti-penicilloyl-bovine serum albumin was partially purified by precipitation with 33% saturated ammonium sulfate. This protein was coupled to microcrystalline cellulose by reaction of the cellulose with carbonyldiimidazole in dioxane, followed by washing and then by reaction with the IgG preparation in borate buffer at pH 9.0 at 4 degrees C. for two days. The cellulose was then washed extensively with PBS and used for preparation of banded strips. Glucose oxidase was also coupled to microcrystalline cellulose in the same manner. A penicilloyl-peroxidase was prepared by first coupling a polyacrylamide amine to HRP, then reacting penicillin G with that preparation. It is believed that the use of a linear polymer as a spacer for attaching the hapten to the enzyme allows more hapten molecules to be coupled to each enzyme molecule and renders the hapten molecules more accessible for binding to antibody, thus speeding the binding rate. Polyacrylamide was synthesized by dissolving 0.5 gm. of acrylamide in 200 ml. of deionized water, degassing, then adding 0.2 ml. of N,N,N',N'-tetramethylethylenediamine and 0.15 gm. of ammonium persulfate. This solution was mixed, then allowed to sit at room temperature for 30 min. then passed through an ultrafiltration membrane, dialyzed vs. deionized water and lyophilized. The polyacrylamide was then dissolved in 1.0 ml. of 0.2 M phosphate buffer at pH 7.7 and 0.3 ml. of 25% glutaraldehyde was added. This solution was incubated at 37 degrees C. for 19 hours after which it was passed through a Sephadex G-25 column to remove the excess glutaraldehyde. The void volume fractions which absorbed strongly at 230 nm were pooled and added to a solution of diaminodipropylamine (0.5 ml. in 2.0 ml. of water) at pH 9.0. This solution was allowed to react at 4 degrees C. over night. The reaction mixture was then passed through a Sephadex G-150 column and the fractions that absorbed significantly at 230 nm. were divided into four pools of equal volume, the second of which was coupled to peroxidase (ERP). HRP was reacted with 1.25% glutaraldehyde at pH 7.0 for 15 hours at room temperature. After passing the reaction mixture through a Sephadex G-25 column, the HRP-containing fractions were pooled and added to the polyacrylamide-diamine preparation, the pH was adjusted to 9.0, and this solution was allowed to react at 4 degrees C. overnight. The peroxidase-polyacrylamide-diamine was then passed through a Biogel P-100 column and the void volume fractions were pooled and concentrated, then reacted with penicillin. Fifty mg. of penicillin G was added to the peroxidase-polyacrylamide-diamine, the pH adjusted to 9.0 and stirred at 4 degrees C. over night. This preparation was then dialyzed extensively, then used for the assay.

Banded strips were prepared by cutting 0.5×8.0 cm. strips of a polyester film having a hydrophilic surface onto which were glued strips of Whatman 3MM chromatography paper. At one end was glued a 0.5×4.0 cm. long paper strip followed by a 3.5 mm. space. Then three one cm. long paper strips were glued onto the Mylar strip with 2.0 mm. spaces between them. The paper on the Mylar was wetted with a solution of 0.02% o-dianisidine in water. The spaces were then filled in with a suspension of microcrystalline cellulose prepared by mixing 50% suspensions of the IgG-cellulose and the glucose oxidase-cellulose in a 20:1 ratio. The first space was filled with 20 ul. of this suspension and the other three spaces each contained 10 ul. These strips were air dried, then stored dry until used.

The strips were developed by placing the end with the longer paper spacer into a small vial containing the developing solution. This solution contained peroxidase-polyacrylamide-diamine-penicillin (25 ul. of a 0.25 microgram/ml. solution), glucose (0.3 ml of a 1.125% glucose solution in 0.2M phosphate buffer at pH 6.0) and 10 ul. of dilutions of penicilloyl-aminocaproic acid (EAC) in water. Under these conditions, pink bands could readily be observed after 20–30 min., such that, with no penicilloyl-EAC in the developing solution, one band was colored; with 0.4 micromolar hapten (penicilloyl-EAC), two bands were colored; and with 1.0 uM penicilloyl-EAC, all three bands were colored.

If needed or desired, antibody to peroxidase, an HRP-binding lectin or some other binder or inactivator of peroxidase can be included in the spacer layers for the purpose of improving the sharpness or decisiveness of zone color determinations. Furthermore, catalase immobilized in the spacer layers may permit more rapid color development in the reaction zones without generation of color in the spacer layers.

EXAMPLE VIII

Banded strips are prepared according to Example VII, except that all of the components of the assay except the sample to be tested are incorporated into the strip. The peroxidase-polyacrylamide-diaminepenicillin is dissolved in a solution of between 0.5 and 1.0% gelatin containing 2.5% glucose and 0.2 M phosphate buffer at pH 6.0, 0.1 ml. of which is applied to the bottom paper strip and dried. In this example, therefore, the user has only to dip the strip into a solution suspected of containing the analyte, wait for a prescribed time, then read the results by counting the number of colored bands on the strip.

EXAMPLE IX

Assay columns are prepared according to Example III, except that the reaction zones are composed of a mixture of IgG-agarose and glucose oxidase-agarose (20:1). Peroxidase-penicillin (as prepared in Example VII), glucose, o-dianisidine, and phosphate buffer, stored in dry form, are dissolved in 1.0 ml of the test sample which is then added to the column and allowed to flow through. The results are read after the prescribed time by counting the number of colored bands on the column. The reagents added to the analyte test sample can be in the form of a small pellet or can be dried onto the under surface of the cap for a small vessel used to measure the volume of sample, etc. In the latter case, the vessel is filled, the cap placed on top, the vessel inverted a few times and the sample is poured into the column. The reagents to be mixed with the sample can even be dried onto a small plug that is stored in the top of the column, in which case they dissolve when the sample is added to the column.

Various other enzyme pairs can be used for generating color in the reaction zones. For example, alkaline phosphatase can be immobilized in the reaction zones with beta-galactosidase coupled to the analyte. The use of naphthol-beta-D-galactopyranoside-6-phosphate as substrate for the alkaline phosphatase results in the generation of naphthol-beta-D-galactopyranoside, which is hydroloyzed by beta-galactosidase to produce naphthol which in the presence of a diazonium salt results in a colored product in the reaction zones.

The accuracy and reliability of the apparatus of the invention depends to some extent upon how readily or easily the generation of color or other detectable change in the different reaction zones may be ascertained. A reaction zone in the direction of analyte flow desirably should show detectable changes only when a significant, minimum quantity of analyte or other material being detected has passed through the preceeding reaction zone; since the physical nature of the apparatus often does not permit reaction to go fully to completion in each such zone, a small "tail" e.g., trace, amount of material may flow into successive zones and may be marginally detected in such zones to yield readings that are difficult to interpret. One may largely avoid this problem, however by several means. Detectors may be employed that are sensitive only to minimum concentrations of a chemical moiety to be detected. For example, one may utilize o-phenylene diamine in place of o-dianisidine as a chromophore in the above examples, the former being less sensitive. Another method involves the placement in spacer layers or, less desirably, in reaction zones, of small quantities of "scavenger" reactants capable of immobilizing or deactivating trace amounts of materials, as exemplified in Example VII. This enables the sensitivity and operation of the apparatus to be tailored as desired to particular analyses. Control of sensitivity and reliability also may depend upon the concentration of the reactant in the solid reaction zones, and the solubility of materials such as the colored product in some analyses.

While a preferred embodiment of the present invention has been described, it should be understood that various changes, adaptations and modifications may be made therein without departing from the spirit of the invention and the scope of the appended claims.

What is claimed is:

1. A device for detecting the presence of an analyte in a carrier liquid suspected of containing said analyte, which device comprises a liquid permeable solid medium which defines a path for fluid flow capable of supporting capillary flow, along which are i) a site for application of the carrier liquid, ii) a diffusively bound labeled reactant specific for the analyte or a chemical moiety which is itself the reaction product of the analyte with another chemical moiety, said labeled reactant being capable of flow along the flow path, wherein said diffusively bound labeled reactant and said analyte or chemical moiety are of a specific ligand-anti ligand pair, and iii) one or more zones spaced along said flow path, each zone having a predetermined amount of a reactant bound to it which is specific for either the analyte or a chemical moiety which is itself the reaction product of the analyte with another chemical moiety;

wherein said device can be used by contacting a carrier liquid with said application site in such a manner that permits said liquid to pass along the flow path by capillary flow such that analyte or reaction product of the analyte with another chemical moiety becomes bound to both the labeled reactant and the reactant bound to the solid medium; and wherein the labeled reactant, with the reactant bound to the solid medium, sandwiches the analyte or a chemical moiety which is itself the reaction product of the analyte with another chemical moiety.

2. A device according to claim 1 wherein said labeled reactant is labeled with an enzyme and is detected by adding a substrate for said enzyme.

3. A device according to claim 1 wherein said site for application of said carrier liquid is a well into which said carrier liquid is placed.

4. A device according to claim 3 which is adapted such that said carrier liquid is drawn out of said well by the capillary action of said liquid permeable solid medium.

5. A device according to claim 1 further comprising a chemical moiety diffusively bound along said flow path, said moiety being capable of reacting with said analyte in order to form a reaction product.

6. A device according to claim 1 wherein said solid permeable medium contains all the materials needed for detecting the presence of said analyte so that all that is required is the application of said carrier liquid.

7. A method for detecting the presence of an analyte in a carrier liquid suspected of containing said analyte, which method comprises;

a) providing a liquid permeable solid medium which defines a path for fluid flow capable of supporting capillary flow, along which are i) a site for application of the carrier liquid, ii) a diffusively bound labeled reactant specific for the analyte or a chemical moiety which is itself the reaction product of the analyte with another chemical moiety, said labeled reactant being capable of flow along the flow path, wherein said diffusively bound labeled reactant and said analyte or chemical moiety are of a specific ligand-anti ligand pair, and iii) one or more zones spaced along said flow path, each zone having a predetermined amount of a reactant bound to it which is specific for either the analyte or a chemical moiety which is itself the reaction product of the analyte with another chemical moiety;

b) contacting said application site with said carrier liquid such that the liquid passes along the flow path by capillary flow such that analyte or reaction product of the analyte with another chemical moiety becomes bound to both the labeled reactant and the reactant bound to the solid medium; and c) detecting the labeled reactant which, together with the reactant bound to the solid medium, has sandwiched the analyte or chemical moiety as an indication of the presence of analyte.

8. A method according to claim 7 wherein said labeled reactant is labeled with an enzyme and is detected by adding a substrate for said enzyme.

9. A method according to claim 7 wherein said site for application of said carrier liquid is a well into which said carrier liquid is placed.

10. A method according to claim 9 which is adapted such that said carrier liquid is drawn out of said well by the capillary action of said liquid permeable solid medium.

11. A method according to claim 7 wherein said solid permeable medium contains all the materials needed for detecting the presence of said analyte so that all that is required is the application of said carrier liquid.

12. A method according to claim 7 wherein said carrier liquid passes as a single material in a single pass.

* * * * *